(12) United States Patent
Ziebert

(10) Patent No.: US 12,042,359 B2
(45) Date of Patent: Jul. 23, 2024

(54) ORTHOPEDIC CAST VENTILATOR

(71) Applicant: Elemental Orthopedics, LLC, Spokane, WA (US)

(72) Inventor: Philip Ziebert, Marcola, OR (US)

(73) Assignee: Elemental Orthopedics, LLC, Spokane, WA (US)

(*) Notice: Subject to any disclaimer, the term of this patent is extended or adjusted under 35 U.S.C. 154(b) by 547 days.

(21) Appl. No.: 17/157,413

(22) Filed: Jan. 25, 2021

(65) Prior Publication Data
US 2021/0228419 A1   Jul. 29, 2021

Related U.S. Application Data

(60) Provisional application No. 62/965,654, filed on Jan. 24, 2020.

(51) Int. Cl.
*A61F 13/04*   (2006.01)
*A61F 5/01*   (2006.01)

(52) U.S. Cl.
CPC .............. *A61F 13/046* (2013.01); *A61F 5/01* (2013.01)

(58) Field of Classification Search
CPC ................................. A61F 13/046; A61F 5/01
USPC .......................................................... 602/14
See application file for complete search history.

(56) References Cited

U.S. PATENT DOCUMENTS

| | | | |
|---|---|---|---|
| 3,908,642 A * | 9/1975 | Vinmont | A61H 9/0078 601/149 |
| 3,998,220 A | 12/1976 | Cleer | |
| 4,387,710 A * | 6/1983 | Beatty, III | A61F 13/046 602/14 |
| 5,837,207 A | 11/1998 | Summers | |
| 6,053,882 A | 4/2000 | Johansen | |
| 6,547,751 B1 | 4/2003 | Barberio | |
| 7,229,425 B2 | 6/2007 | Dunagan | |
| 7,270,642 B2 * | 9/2007 | Ouchene | A61F 13/085 128/DIG. 20 |
| 7,828,757 B2 | 11/2010 | Blocker | |
| 8,231,561 B2 * | 7/2012 | Siegner | A61F 13/046 128/DIG. 20 |
| 9,393,354 B2 | 7/2016 | Freedman | |
| 9,615,957 B2 | 4/2017 | Barberio | |
| 10,245,545 B2 | 4/2019 | Hara | |

(Continued)

FOREIGN PATENT DOCUMENTS

CA   2103530 A1   2/1994
CN   203336748 U   12/2013

(Continued)

OTHER PUBLICATIONS

Webpage: http://www.castcooler.com/castcooler_works.html (accessed Oct. 14, 2019).

*Primary Examiner* — Kim M Lewis
(74) *Attorney, Agent, or Firm* — Randall Danskin P.S.

(57) ABSTRACT

An orthopedic cast ventilator apparatus and related methods are provided. The cast ventilator includes an air pump disposed within a housing connected to an air delivery cuff via tubing. The air pump draws air into the air mover through a primary air filter and through an air intake aperture. The air pump also pumps air out through a discharge port in the housing, through a length of tubing, through a secondary air filter, and into an air delivery cuff. The cleaned air fills two arms of the air delivery cuff and is forced out through cuff discharge ports.

9 Claims, 6 Drawing Sheets

(56) References Cited

U.S. PATENT DOCUMENTS

| | | | |
|---|---|---|---|
| 2004/0162511 A1* | 8/2004 | Barberio | A61F 5/01 |
| | | | 602/14 |
| 2008/0183115 A1 | 7/2008 | Pierce | |
| 2008/0312570 A1 | 12/2008 | Dunagan | |
| 2009/0198160 A1 | 8/2009 | Coyne | |
| 2013/0072837 A1* | 3/2013 | Rousso | A61F 5/0104 |
| | | | 601/152 |
| 2013/0174741 A1 | 7/2013 | Kaddour | |
| 2013/0238042 A1 | 9/2013 | Gildersleeve | |
| 2021/0001019 A1* | 1/2021 | Elder | A61F 13/0216 |

FOREIGN PATENT DOCUMENTS

| | | |
|---|---|---|
| CN | 106855263 A | 6/2017 |
| CN | 209246268 U | 8/2019 |

\* cited by examiner

ORTHOPEDIC CAST VENTILATOR

FIELD

The present invention relates generally to apparatus and related methods for epidermal irritation relief. More specifically, the present invention is concerned with an orthopedic cast ventilator configured to provide filtered, purified, and/or medicament-added air to a gap between the cast and the skin of the wearer to decrease the number and severity of complications that may arise due to lack of air circulation in that region.

BACKGROUND

This invention combats cellulitis, necrotizing fasciitis, gangrene, toxic shock syndrome, skin necrosis, compartment syndrome, abscesses, and itching. By combating itching, the problem of creating infections is decreased by decreasing the impulse to insert foreign objects to scratch the itch. This invention also decreases the exposure of the limb to pollen, dander, dust, fungi spores, allergens, and pathogens.

By forcing clean air through the narrow air gap between the cast and the skin of the wearer, the problems associated with an orthopedic cast are relieved or eliminated. The Mayo Clinic and Cleveland Clinic currently recommend to set a blow dryer on a cool setting and hold to the cast opening to try to force air through. Other cast ventilation products operate off a vacuum which draws contaminants from the environment through the cast. The present invention utilizes positive pressure (rather than negative pressure) and purified air with a manifold system designed to fit into one opening of the cast to create increased and improved air flow and decrease the problems associated with orthopedic casts.

SUMMARY

The present invention comprises an orthopedic cast ventilator apparatus. The cast ventilator includes a housing connected to an air delivery cuff via tubing. An electric air pump is located within the housing and is connected to a power supply and a power switch. The air pump draws air into the housing through an air intake aperture and passing through a primary air filter. The air pump pumps air out of the housing through a discharge port. The air is pumped out through the housing discharge port, through a length of tubing, through a secondary air filter, and into an air delivery cuff. The cleaned air fills the arms of the air delivery cuff and is forced out through cuff discharge ports.

The foregoing and other objects are intended to be illustrative of the invention and are not meant in a limiting sense. Many possible embodiments of the invention may be made and will be readily evident upon a study of the following specification and accompanying drawings comprising a part thereof. Various features and subcombinations of invention may be employed without reference to other features and subcombinations. Other objects and advantages of this invention will become apparent from the following description taken in connection with the accompanying drawings, wherein is set forth by way of illustration and example, an embodiment of this invention and various features thereof.

BRIEF DESCRIPTION OF THE DRAWINGS

A preferred embodiment of the invention, illustrative of the best mode in which the applicant has contemplated applying the principles, is set forth in the following description and is shown in the drawings and is particularly and distinctly pointed out and set forth in the appended claims.

DETAILED DESCRIPTION

As required, one or more detailed embodiment of the present inventive concept is disclosed herein; however, it is to be understood that the embodiments disclosed are merely exemplary of the principles of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
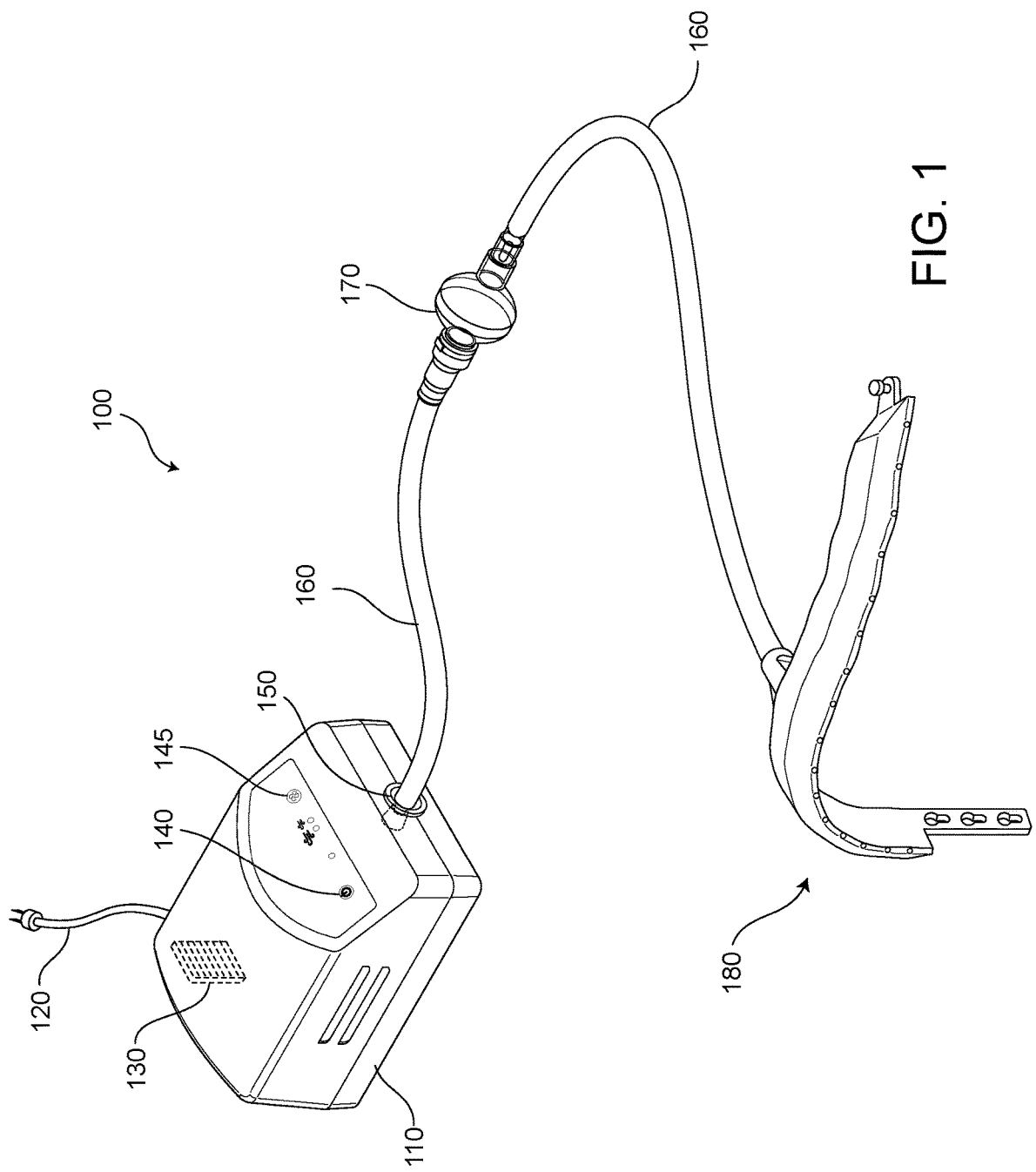
FIG. 1 is an embodiment of an orthopedic cast ventilator apparatus.

Referring to FIG. 1, in one embodiment, an orthopedic cast ventilator apparatus 100 includes a housing 110 with a discharge port 150 in air-sealed connection with an air delivery cuff 180 via tubing 160. According to FIG. 1, the housing 110 is electrically connected to a power supply 120. In some embodiments, the power supply 120 is alternating current and in some other embodiments, the power supply 120 is direct current battery. The housing 110 includes a main power switch 140 configured to be selectively actuated between an unpowered position and one or more powered positions. In the embodiments shown in FIG. 1, the housing 110 also includes a fan speed selector switch 145. In some embodiments, the housing further includes an AC/DC transformer (147, shown in FIG. 2) in electrical connection with the power supply 120 and an air pump (190, shown in FIG. 2). In some embodiments, the housing further includes a PCB controller (148, shown in FIG. 2) in electrical connection with the power supply 120 and the air pump (190, shown in FIG. 2). The housing 110 is configured to selectively electrically engage the air pump (190, shown in FIG. 2) when the power switch 140 is actuated to one of the powered positions. The housing 110 is configured to selectively electrically disengage the air pump (190, shown in FIG. 2) when the power switch 140 is actuated to the unpowered position. In some embodiments, the one or more powered positions of the power switch 140 correspond with one or more selectively variable speeds of the air pump (190, shown in FIG. 2) and also correspond with one or more selectively variable rate of air pumped through the tubing 160. In some embodiments, the fan speed selector switch 145 controls the rate of air pumped by the air pump 190 through the tubing 160. In some embodiments, the power to the air pump 190 is disengaged automatically by the PCB controller 148 after a predetermined period of time.

Continuing to refer to the embodiment shown in FIG. 1, the housing 110 includes a discharge port 150. The housing discharge port 150 forms an air-sealing connection between the air pump (190, shown in FIG. 2) and the tubing 160. In some embodiments, the discharge port 150 includes a quick connector fitting (not shown). In some embodiments, the air mover discharge port 150 includes hose barbs (not shown).

In the embodiment shown in FIG. 1, the tubing 160 includes a secondary air filter 170. Preferably, the secondary air filter 170 is in-line in the tubing 160. In other words, preferably, the secondary air filter 170 is in air sealing connection with the interior of the tubing 160 such that air moving from air pump (190, shown in FIG. 2) to the air delivery cuff 180 must pass through the secondary air filter 170. In some embodiments, the secondary air filter 170 includes opposite ends and is connected to tubing 160 at each of the opposite ends. In some embodiments, the secondary air filter 170 is connected to the air mover discharge port 150 at one end and to tubing 160 at the opposite end. In some embodiments, the secondary air filter 170 is connected to tubing 160 at one end and to the air delivery cuff 180 at the opposite end. In any event, air from the air pump 190 being pumped to and out through the air delivery cuff 180 must pass through the secondary air filter 170. Preferably, the secondary air filter 170 is antiviral, antibacterial, and antifungal. In some embodiments, the secondary air filter 170 is configured to administer one or more medicament.

Figure 2:
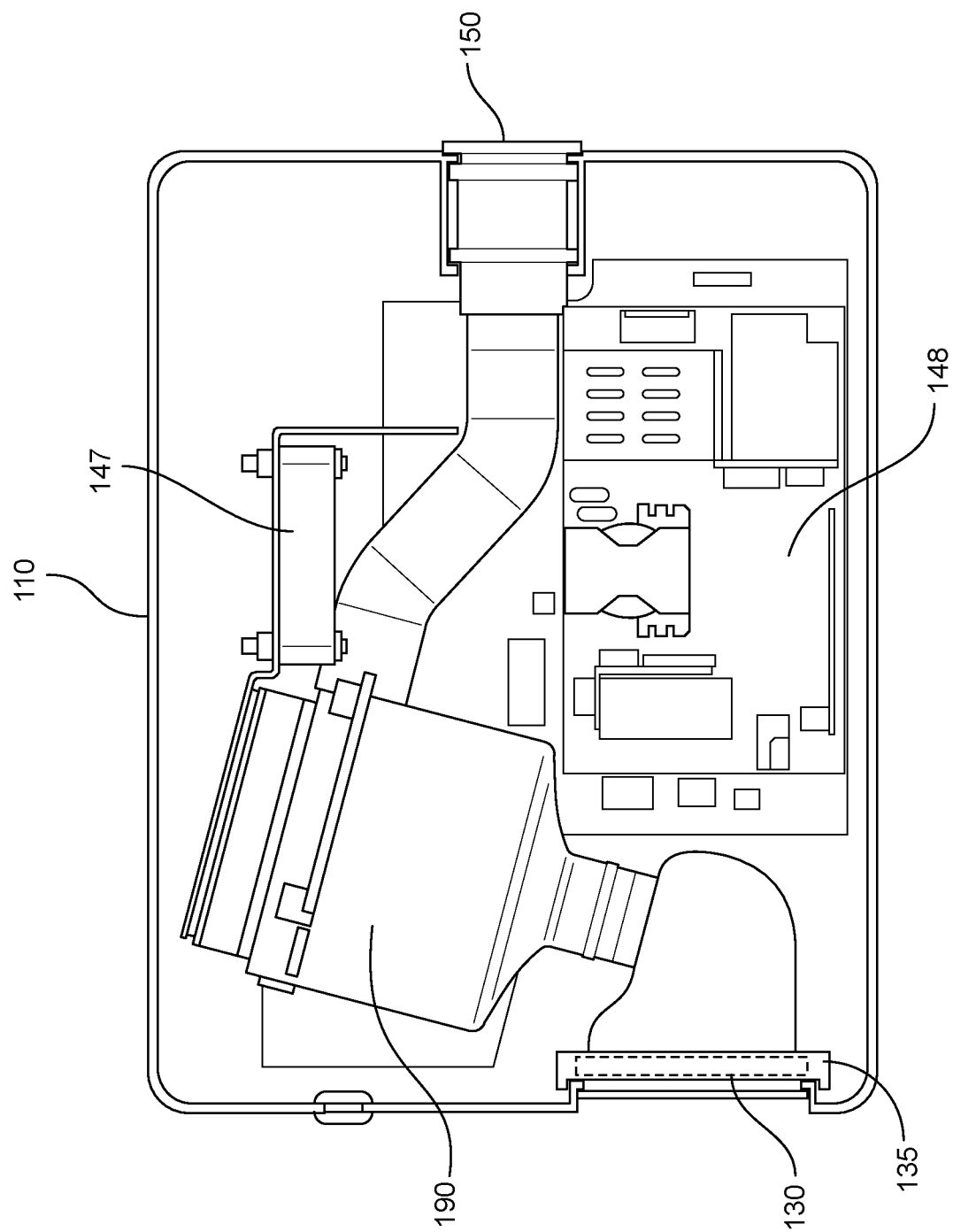
FIG. 2 is an interior view of the housing of the orthopedic cast ventilator apparatus of FIG. 1.

Referring to FIG. 2, one embodiment of the interior of the housing 110 is shown. As discussed above, the housing 110 is electrically connected to a power supply (120, shown in FIG. 1). The housing 110 includes a main power switch (140, shown in FIG. 1) configured to be selectively actuated between an unpowered position and one or more powered positions. The housing 110 is configured to selectively electrically engage the air pump 190 when the power switch 140 is actuated to one of the powered positions. The housing 110 is configured to selectively electrically disengage the air pump 190 when the power switch 140 is actuated to an unpowered position. The one or more powered positions of the power switch 140 correspond with one or more selectively variable speeds of the air pump 190 and also correspond with one or more selectively variable rate of air pumped through the tubing 160. In some embodiments, the housing 110 also includes a fan speed selector switch (145, shown in FIG. 1). In some embodiments, the housing further includes an AC/DC transformer 147 in electrical connection with the power source (120, shown in FIG. 1) and the air pump 190. In some embodiments, the housing further includes a PCB controller 148 in electrical connection with the power source (120, shown in FIG. 1) and the air pump 190.

As shown in FIG. 2, the air pump 190 is in air-sealing connection with the air intake aperture 135 and with the discharge port 150. FIG. 2 also shows the primary air filter 130 situated at and in air-sealing connection with the air intake aperture 135 of the housing 110. Air draw into the housing 110 through the air intake aperture 135 is forced to pass through a primary air filter 130 situated at the air intake aperture 135. Preferably, the primary air filter 130 is configured to filter particulates of a predetermined size and/or shape from the air before the air is drawn into the housing 110. Preferably, the primary air filter 130 is a high-efficiency particulate air (HEPA) filter. In some embodiments (not shown), the housing 110 includes a plurality of air intake apertures 135.

Figure 3:
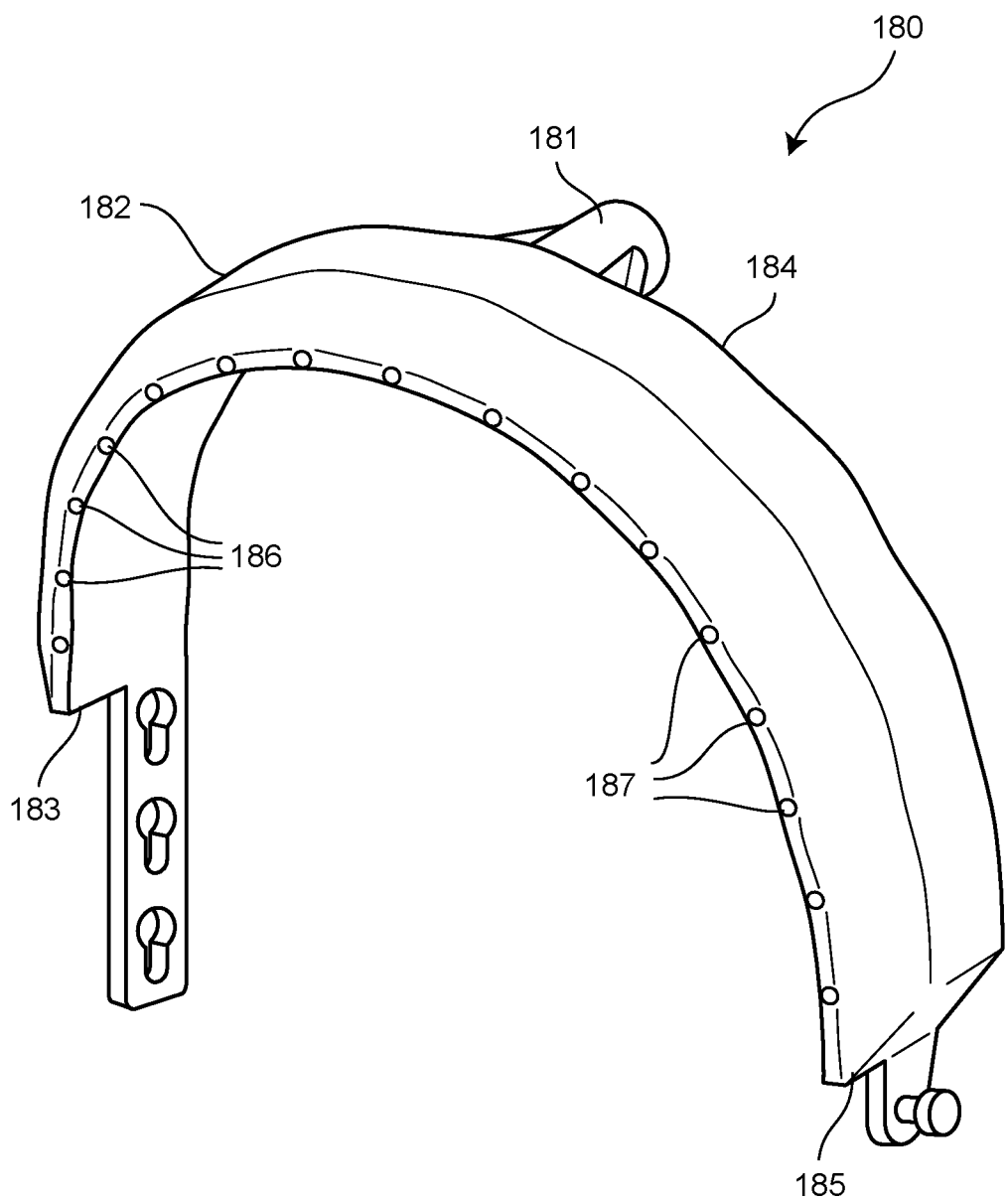
FIG. 3 is an embodiment of an air delivery cuff.

Referring to FIG. 3, an embodiment of the air delivery cuff 180 is shown. In the embodiment of FIG. 3, the air delivery cuff 180 includes a clean air intake port 181. The air delivery cuff 180 also includes a first cuff elongated extension arm 182 and a second cuff elongated extension arm 184. The first cuff elongated extension arm 182 is opposite the second cuff elongated extension arm 184 with the clean air intake port 181 disposed between the first and second elongated extension arms 182 and 184. The first and second cuff elongated extension arms 182 and 184 are made of a flexible material having an internal cavity configured to take a first shape and form when a portion of air is evacuated. The first and second cuff elongated extension arms 182 and 184 are further configured to take a second shape and form when the internal cavity is filled with air or otherwise having internal air pressure greater than when the internal cavity has taken its first shape and form with the air evacuated therefrom. The first elongated extension arm 182 includes a distal end 183 which is air-sealed. The second elongated extension arm 184 includes a distal end 185 which is air-sealed.

Continuing to refer to FIG. 3, the first elongated extension arm 182 includes one or more cuff discharge ports 186. The second elongated extension arm 184 includes one or more cuff discharge ports 187. The air delivery cuff 180 is configured such that air enters the air delivery cuff 180 through the clean air intake port 181 and exits through the one or more cuff discharge ports 186 and 187. In the embodiment shown in FIG. 3, the one or more cuff discharge ports 186 and 187 are located on the respective first and second elongated extension arms 182 and 184 on a side opposite the clean air intake port 181.

Figure 4:
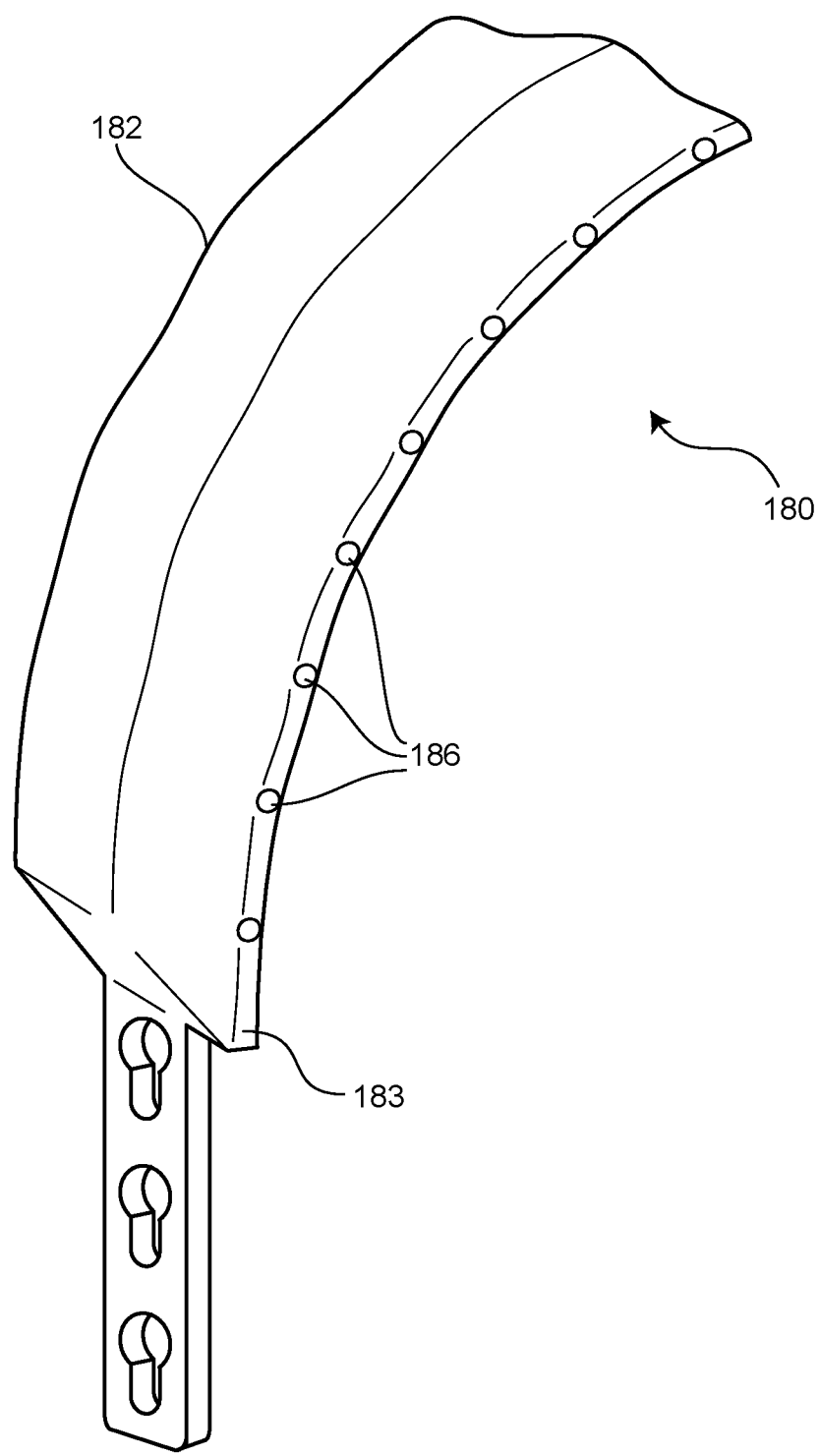
FIG. 4 is an enlarged view of a first arm of the air delivery cuff of FIG. 3.

Referring to FIG. 4, the first elongated extension arm 182 of the air delivery cuff 180 is shown in greater detail. The first elongated extension arm 182 includes distal end 183 and, in the embodiment shown in FIG. 4, three discharge ports 186. The discharge ports 186 are positioned on a side opposite the clean air intake port 181.

Figure 5:
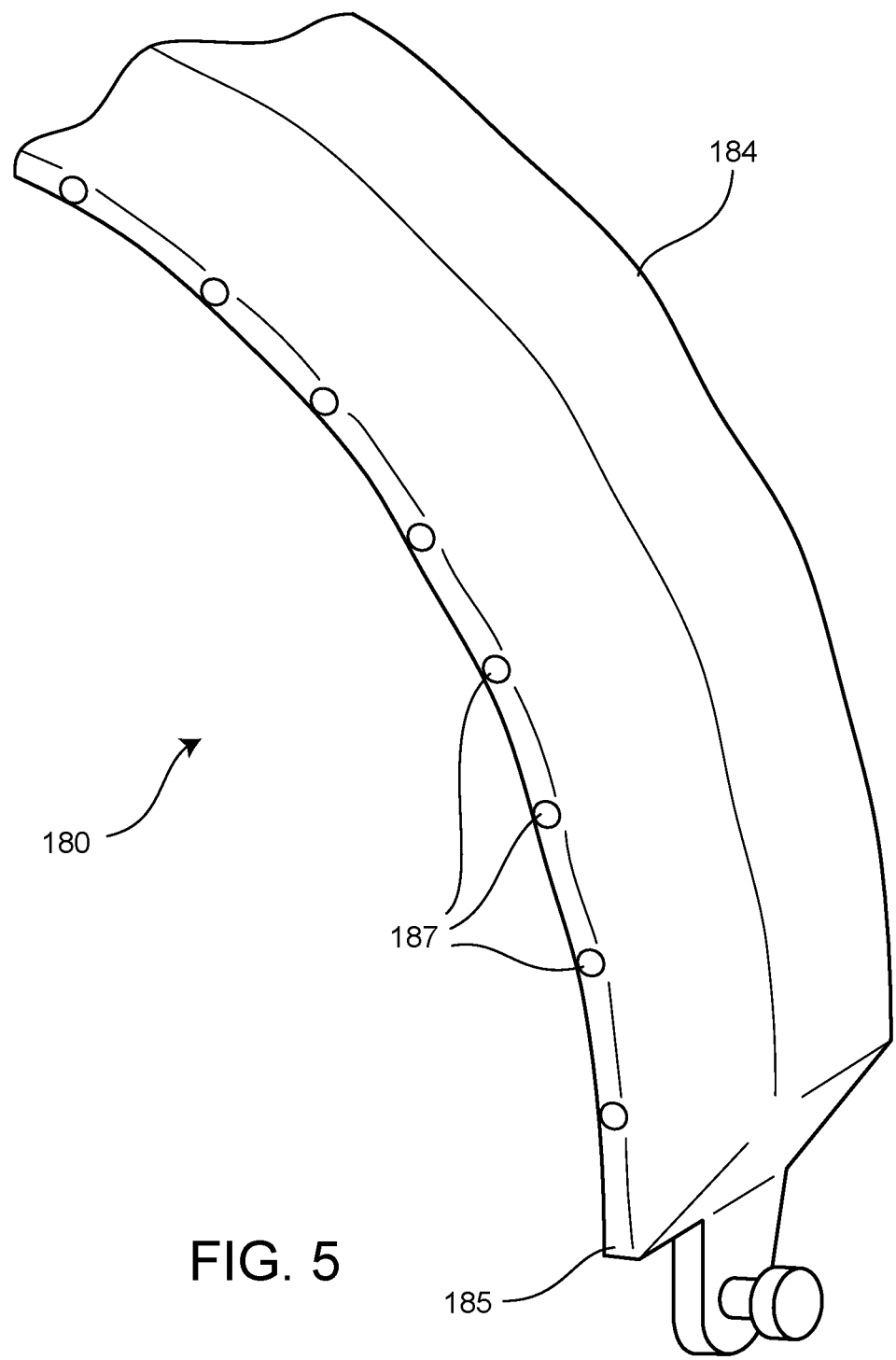
FIG. 5 is an enlarged view of a second arm of the air delivery cuff of FIG. 3.

Referring to FIG. 5, the second elongated extension arm 184 of the air delivery cuff 180 is shown in greater detail. The second elongated extension arm 184 includes distal end 185 and, in the embodiment shown in FIG. 5, three discharge ports 187. The discharge ports 187 are positioned on a side opposite the clean air intake port 181.

Figure 6:
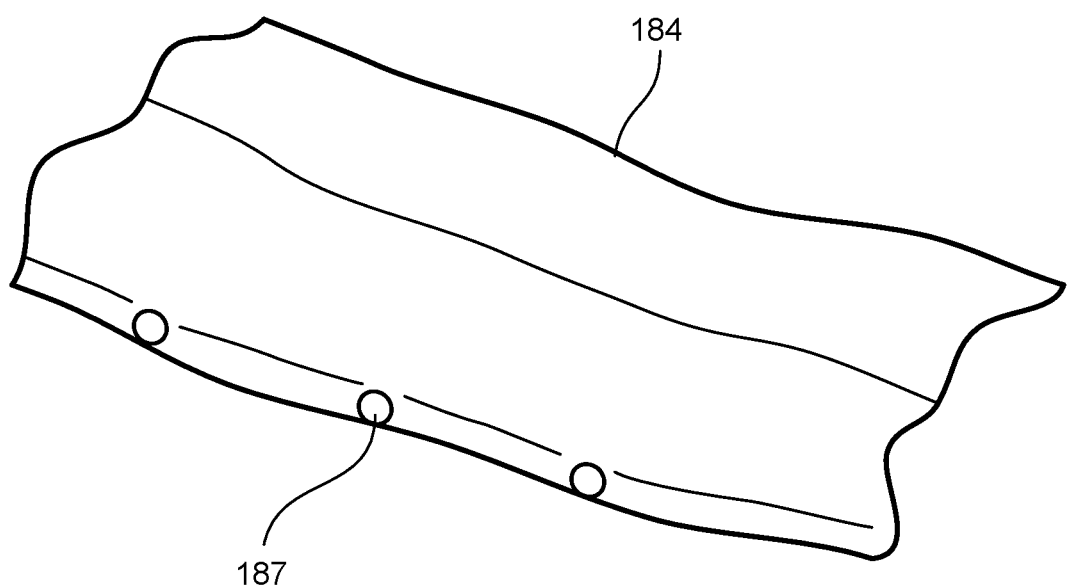
FIG. 6 is an enlarged view of a discharge port on an arm of the air delivery cuff of FIG. 3.

FIG. 6 shows an enlarged view of one of the discharge ports 187 of the second elongated extension arm 184.

To assemble the orthopedic cast ventilator apparatus 100 discussed above, the housing 110 is provided. The housing 110 includes a main power switch 140 at the exterior of the housing 110. The housing 110 also includes an air intake aperture 135 and a discharge port 150 at the exterior of the housing 110. An electric air pump 190 is provided within the housing. The air pump 190 is provided with an air-seal connection between the air intake aperture 135 and the discharge port 150. The air pump 190 and the main power switch 140 are in operable electrical connection with the power supply 120 such that the air pump 190 is electrically engaged when the power switch 140 is actuated to one of the powered positions and the air pump 190 is electrically disengaged when the power switch 140 is actuated to the unpowered position. As discussed above, the power supply 120 is either alternating current or direct current. In some embodiments, a PCB controller 148 is also provided within the housing in operable electrical connection with the main power switch 140 and the air pump 190. The PCB controller 148 is configured to control electrical power to the air pump 190 for a predetermined period of time when the main power switch 140 is actuated to a powered position. The air pump 190 is disengaged from the electrical power supply 120 after the predetermined period of time or when the main power switch 140 is actuated to the unpowered position. In some embodiments, an AC/DC transformer 147 is provided within the housing 110 and in operable electrical connection with the power supply 120, the main power switch 140, and the air pump 190. The AC/DC transformer 147 is configured to transform electrical power between alternating current and direct current.

A primary air filter 130 is provided at the air intake aperture 135. The primary air filter 130 is configured to filter out particulates equal to or greater than a predetermined size. The primary air filter 130 is positioned relative to the air intake aperture 135 such that air drawn into and through the air pump 190 is forced to pass through the primary air filter 130 before entering the air-sealed connection between the air intake aperture 135, the air pump 190, and the discharge port 150.

An air delivery cuff 180, external to the housing 110, is provided. A length of tubing 160 is provided, external to the housing 110, and in air-seal connection between the discharge port 150 and the air delivery cuff 180. A secondary air filter 170 is provided in air-sealed connection with the interior of the tubing 160 and inline along the length of tubing 160 at some point between the discharge port 150 and the air delivery cuff 180 such that air moving from discharge port 150 to the air delivery cuff 180 must pass through the secondary air filter 170.

The air delivery cuff 180 is provided with a clean air intake port 181, a first cuff elongated extension arm 182 and a second cuff elongated extension arm 184, each having a distal end 183 and 185, respectively. The air intake port 181 is in air-sealed connection with the tubing 160. The air delivery cuff 180 is also provided with discharge ports 186 and 187, as discussed above.

In use, the orthopedic cast ventilator apparatus 100 discussed above is provided. The power switch 140 is actuated to the unpowered position or the power source is otherwise disengaged. A portion of the air within the first and second elongated extension arms 182 and 184 of the air delivery cuff 180 is evacuated and the flexible material is flattened to take its first form and shape. The flexible material of the air delivery cuff 180 first and second elongated extension arms 182 and 184 in its flattened first form and shape is wrapped at least partially around an appendage and wedged between an orthopedic cast and the skin of the wearer of the orthopedic cast. In some embodiments, the distal ends 183 and 185 overlap while in some other embodiments, the distal ends 183 and 185 do not overlap.

With the flexible material of the air delivery cuff 180 wedged between the orthopedic cast and the skin of the wearer, the power switch 140 is actuated to one of the one or more powered positions. The air pump 190 is electrically engaged at one of the predetermined selectively variable speeds. The electrically engaged air pump 190 draws air in through the air intake aperture 135 and through the primary air filter 130. The air pump 190 moves air out through the discharge port 150, through the tubing 160, through the secondary air filter 170, and into the air delivery cuff 180. In some embodiments, a fan speed selector 145 is actuated to select the fan speed and control the rate of air flowing through the air pump 190, through the tubing 160, and into the air delivery cuff 180. The internal cavities of the first and second cuff elongated extension arms 182 and 184 are filled with air from the air pump 190 and the first and second cuff elongated extension arms 182 and 184 expand to take their respective second shapes and forms, forming at least a partial air-seal between the orthopedic cast and the wearer. Once the first and second cuff elongated extension arms 182 and 184 of the air delivery cuff 180 takes their respective second shapes and forms, air within the air delivery cuff 180 is released through the discharge ports 186 and 187 and into an air gap between the orthopedic cast and the skin of the wearer. In this manner, clean and purified air, and in some cases, one or more medicament, is delivered to the air gap between the orthopedic cast and the skin of the wearer. This provides itch relief and a drier skin environment.

Because the air delivery cuff 180 is made from a flexible material, it can be positioned and repositioned in many different locations relative to the orthopedic cast and the wearer to provide the desired relief. For example, it can be positioned at the top of the cast or at the bottom of the cast. For longer casts or casts that extend around a joint such as a knee or elbow, if the cast includes an opening, the air delivery cuff 180 can be wedged in such an opening.

In the foregoing description, certain terms have been used for brevity, clearness and understanding; but no unnecessary limitations are to be implied therefrom beyond the requirements of the prior art, because such terms are used for descriptive purposes and are intended to be broadly construed. Moreover, the description and illustration of the present inventive concept is by way of example, and the scope of the invention is not limited to the exact details shown or described.

Although the foregoing detailed description has been described by reference to one or more exemplary embodiment, and the best mode contemplated for carrying out the present inventive concept has been shown and described, it will be understood that certain changes, modification, or variations made in embodying the above invention, and in the construction thereof, other than those specifically set forth herein, may be achieved by those skilled in the art without departing from the spirit and scope of the invention, and that such changes, modification, or variations are to be considered as being within the overall scope of the present invention. Therefore, it is contemplated to cover the present invention and any and all changes, modifications, variations, or equivalents that fall within the true spirit and scope of the underlying principles disclosed and claimed herein. Consequently, the scope of the present invention is intended to be limited only by the attached claims, all matter contained in the above description and shown in the accompanying drawings shall be interpreted as illustrative and not in a limiting sense.

Finally, it will be appreciated that the purpose of the annexed Abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed is:

1. A method of using an orthopedic cast ventilator apparatus, the method comprising:
providing an orthopedic cast ventilator apparatus, the orthopedic cast ventilator apparatus comprising:
a housing comprising:
an air intake aperture and a discharge port;
an air pump electrically connected to a power supply and controlled by a power switch, the power switch is configured to actuate between one or more powered position and an unpowered position, the air pump is in air-seal connection between the air intake aperture and the discharge port; and a primary air filter disposed at the air intake aperture such that air drawn in through the air intake aperture by the air pump is forced through the primary air filter; and an air delivery cuff in air-seal connection with the discharge port of the housing, the air delivery cuff comprising:

a clean air intake port disposed between a first elongated extension arm and a second elongated extension arm, the first elongated extension arm being disposed opposite to the second elongated extension arm, and each of the first and second elongated extension arms having a distal end and one or more discharge port, and each of the first and second elongated extension arms is configured to wrap at least partially around an appendage and wedge between an orthopedic cast and skin of a wearer of the orthopedic cast;

actuating said power switch to an unpowered position;

evacuating a portion of air from an internal cavity within one of the first or second elongated extension arm;

wedging at least a portion of the first or second elongated extension arm of the air delivery cuff into a space between an orthopedic cast and a wearer of said orthopedic cast;

actuating said power switch to a powered position;

electrically engaging said air pump to draw air through the primary air filter and air intake aperture;

pumping air out through the air pump and out through the discharge port;

pumping air through the tubing and secondary air filter;

pumping air into the air delivery cuff;

pumping air into one of the first or second elongated extension arm of the air delivery cuff;

pumping air out through the one or more cuff discharge ports;

evacuating a subsequent portion of air from the internal cavity within one of the first or second elongated extension arm; and repositioning at least a portion of the first or second elongated extension arm of the air delivery cuff into the space between the orthopedic cast and the wearer of said orthopedic cast at a different location.

2. The method of claim 1, wherein said discharge port of said housing is air-seal connected to the clean air intake port of said air delivery cuff via a length of tubing.

3. The method of claim 1, further comprising a secondary air filter disposed between the discharge port of the housing and the clean air intake port of the air delivery cuff.

4. The method of claim 2, further comprising a secondary air filter disposed inline along the length of tubing, between the discharge port of the housing and the clean air intake port of the air delivery cuff.

5. The method of claim 1, wherein the housing further comprises a fan speed selector switch in operable electrical connection with the air pump and the power supply and configured to control the rate of air flow through the air pump.

6. The method of claim 1, wherein the housing further comprises an AC/DC transformer in operable electrical connection with the air pump and the power supply and configured to convert AC power to DC power.

7. The method of claim 1, wherein the housing further comprises a PCB controller in operable electrical connection with the air pump, the power supply, and the power switch, the PCB controller is configured to automatically electrically disengage the air pump from the power supply after a predetermined period of time after the power switch has been actuated to one of the one or more powered positions.

8. The method of claim 1, wherein each of the first elongated extension arm and the second elongated extension arm of the air delivery cuff are made of a flexible material, and each of the first elongated extension arm and the second elongated extension arm of the air delivery cuff have an internal cavity configured to take a first shape and form when a portion of air is evacuated from the internal cavity, and configured to take a second shape and form when the internal cavity is filled with air.

9. The method of claim 1, wherein each of the one or more discharge ports of each of the first and second elongated extension arms are positioned on a side of the air delivery cuff opposite the clean air intake port.

* * * * *